United States Patent [19]

Friese et al.

[11] Patent Number: 5,087,422
[45] Date of Patent: Feb. 11, 1992

[54] WICKBOLD COMBUSTION APPARATUS AND KIT FOR THIS APPARATUS

[75] Inventors: Hans-Jochen Friese, Dulmen; Aribert Pukropski, Marl, both of Fed. Rep. of Germany

[73] Assignee: Hüls Aktiengesellschaft, Marl, Fed. Rep. of Germany

[21] Appl. No.: 171,136

[22] Filed: Mar. 16, 1988

Related U.S. Application Data

[63] Continuation of Ser. No. 922,845, Oct. 24, 1986, abandoned.

[30] Foreign Application Priority Data

Dec. 19, 1985 [DE] Fed. Rep. of Germany ... 8535732[U]

[51] Int. Cl.$^5$ ............................................. G01N 31/12
[52] U.S. Cl. ......................................... 422/61; 422/78; 422/99; 422/101; 422/103; 285/911
[58] Field of Search ............... 422/61, 78, 99, 101, 422/103; 285/911, DIG. 12

[56] References Cited

U.S. PATENT DOCUMENTS 3,544,281 12/1970 Phillips ............................. 285/911 X
3,667,785 6/1972 Kapeker ........................... 285/911 X

FOREIGN PATENT DOCUMENTS 2527618 1/1975 Fed. Rep. of Germany .
2816768 7/1978 Fed. Rep. of Germany .
762597 11/1956 United Kingdom .

OTHER PUBLICATIONS

Treatise on Analytical Chemistry, Part I, 2nd Ed., vol. 5, Theory & Practice, Elving et al., p. 31, 1982.
Treatise on Anal. Chem., Part II, Anal. Chem. of Inorganic & Organic Compounds, vol. 12, Kolthoff et al., pp. 194-195, 1965.
"ASTM, ANSI/ASTM D2785-70 (Reapproved 1975), Standard Test Method for Trace Quantities of Total Sulfur..." pp. 688-703.
Angen. Chem. 64, Jahrg. 1952, Nr. 5, Wickbold, "Neue Schnellmethode zur Halogenbestimmung in Organischen Substanzen", pp. 133-135, 1952.
Angew. Chem. 66. Jahrg. 1954, Nr. 6, Wickbold, "Die Quantitative Verbrennung Fluor-Haltiger Organischer Substanzen", pp. 173-174, 1954.
Ehrenberger, "Die Wickbold-Apparatus", G-I-T Fachz Lab. 21, Jg. Sep. 11, 1977.
Wheaton Scientific Pamphlet, "The Wheaton Connection", 1970.
Ullman, Band 5, 1980.
Ehrenberger and Gorbach: Methoden der Organischen Elementarund Spurenanalyse, Weinheim 1973; pp. 229-243.

*Primary Examiner*—Lynn Kummert
*Attorney, Agent, or Firm*—Oblon, Spivak, McClelland, Maier & Neustadt

[57] ABSTRACT

The kit includes a U-shaped cooling part containing a coil condenser, various combustion chambers with or without water cooling, burners, sample containers, and separating receivers. Almost all of the parts are made of quartz. The parts are assembled by ground joints. The axes of the combustion part and the cooling and absorption part run parallel to one another and are vertical. In the various combustion apparatus assemblable from the kit, all substances can be burned completely and without trouble. The apparatus can easily be rearranged and optimally suited to each combustion task.

6 Claims, 4 Drawing Sheets

WICKBOLD COMBUSTION APPARATUS AND KIT FOR THIS APPARATUS

This application is a continuation of application Ser. No. 922,845, filed on Oct. 24, 1986, now abandoned.

FIELD OF THE INVENTION

The invention relates to a Wickbold combustion apparatus for testing for halogens, sulfur, and other elements in organic and inorganic samples.

BACKGROUND OF THE INVENTION

In combustion apparatuses many materials are converted to simple, analytically well determinable inorganic compounds by combustion in excess oxygen. The apparatus must be so designed that solid, liquid, and gaseous samples can be completely burned in it. It is desirable that the spatial arrangement of the apparatus should be compact.

It is known to use combustion apparatus of the type known generically as Wickbold apparatus to meet these requirements. Such an apparatus consists of a cold combustion space, a condenser, an absorption device, and a burner. The cold combustion space and the condenser form a unit and are placed at right angles to one another, while the burner and the absorption device are connected by ground glass joints. Solid, liquid, and gaseous samples can be burned (G-I-T, Fachz. Lab., 21. Jg. Sept. 11, 1977, pages 944–950).

Strongly soot-forming or sublimating samples such as organometallic or silicon compounds cannot be completely burned with the usual apparatus. Alkali-containing samples quickly result in destruction of the testing apparatus, especially of the burner. Moreover, the usual apparatus requires a large space and demands a time-consuming rearrangement when tasks are changed.

OBJECT OF THE INVENTION

The object of the invention is to provide a Wickbold apparatus with which each combustion task can be performed, which is simple to manufacture, which is compact, which is clearly organized, and which allows a fast rearrangement of the component parts.

SUMMARY OF THE INVENTION

This object is achieved according to the invention by a kit from the parts of which the apparatus most suited for each combustion task can be put together. The kit contains various combustion chambers and absorption receivers which, in use, are combined with a cooling part. The combustion part of the apparatus, consisting of a burner and a combustion chamber, is vertical and placed parallel to the cooling and absorption part.

DETAILED DESCRIPTION OF THE PRESENTLY PREFERRED EMBODIMENT OF THE INVENTION

Figure 1:
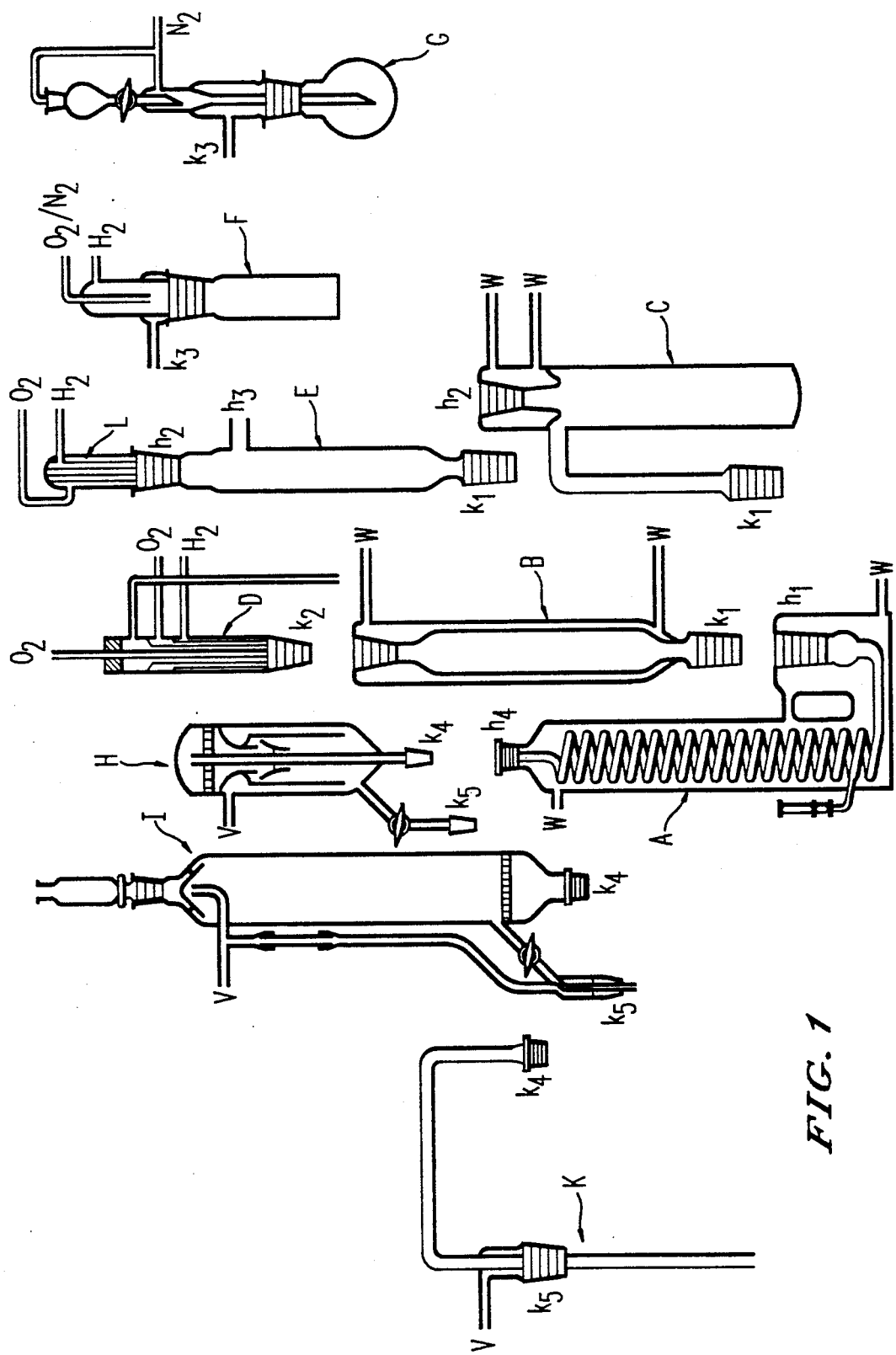
FIG. 1 is a side view of the components of the kit.

A kit comprising a first embodiment of the invention is made up of the parts represented in FIG. 1, namely:

A: a cooling part containing a coil condenser;

B: a combustion chamber with a gas intake and a gas outlet on its opposite ends;

C: a combustion chamber with a gas intake and a gas outlet on the water-cooled end:

D: a suction burner with suction capillaries and an adjustable annular clearance;

E: a combustion chamber with a gas intake and a gas outlet on its opposite ends and with a lateral adapter;

F: a sample container with an attachment for gasification or pyrolysis of solid and liquid samples or for attachment of a sample bell with a removable base plate;

G: a sample container with an attachment for determination of boron in solids;

H: a short separating receiver with a 3-way cock in the discharge line;

I: a long separating receiver with a 2-way cock in the discharge line and an overflow device;

K: a vacuum adapter for connection of receivers; and

L: a burner without suction capillaries.

Other apparatus and auxiliary devices available in the laboratory (such as measuring flasks, hoses, stands, and clamps) are not enumerated or illustrated.

Parts A, B, C, E, F, and G are made of boron-free material, preferably quartz or ceramic. The burners D and L are made of quartz, ceramic, or metal. The separating receivers H and I can be made of soft soda glass or chemically resistant plastic. A separating receiver free of boron material is necessary only for determination of boron. The vacuum adapter K is made of a material resistant to hydrofluoric acid (e.g., a plastic such as polyethylene or polytetrafluoroethylene). In use, the vacuum adapter K is connected to a receiver made of a material resistant to hydrofluoric acid.

The cooling part A is bent in the shape of a capital U and optionally can be made of two parts, one a water-cooled U-shaped bottom part made of quartz with two upwardly open connections (e.g., sockets) and a coil condenser (optionally made of soft soda glass) with a cone on the lower end.

The combustion chamber B is water-cooled. In use, the combustion chambers C and E are suspended in the air space in the combustion apparatus and are cooled by the surrounding air. Metals can optionally be deposited in a mirror like fashion on the inside wall of these chambers. If other deposits form there, they can optionally be removed by heating of the combustion chambers with an open flame from the outside.

The sample container F can have a flat or a spherical bottom. It can also consist of a downwardly open bell which is closed with a removable hermetic base plate.

The short separating receiver H contains a 3-way cock in the discharge line. The 3-way cock can be used to discharge the liquid separated in the separating receiver H into a receiver. Alternatively, the separating receiver H can be cut off from the receiver and at the same time the receiver can be aerated. Accordingly, a low pressure (e.g., 0.3 to 0.9 bar absolute) in the apparatus can be maintained.

The long separating receiver I contains a 2-way cock in the discharge line. The 2-way cock can be used to discharge the liquid present in the separating receiver I into a receiver. Alternatively, the separating receiver I can be cut off from the receiver. To the separating receiver I, an overflow device is laterally fastened. The overflow device consists of a pipe between the point of connection with the separating receiver I and a vacuum connection. Thus, the pipe consists partially of a capillary or contains another cock.

The burner L is not absolutely necessary. In the burner D, the adjustable annular clearance can be closed, as a result of which the burner D is functionally converted into the burner L. The burner L is more simply designed than the burner D. However, the burner D is suitable for all combustion tasks.

The components in the separating receivers H and I, the details for construction of the burners D and L, and also the embodiment of the attachments on the sample containers F and G are known.

In use, an absorption solution can be charged into the long separating receiver I from above. A connection for addition of absorption solution into the cooling coil can be present on the lower end of the cooling coil of the cooling part A.

The parts of the kit are preferably assembled by ground connections. Specifically, sockets (h) and cones (k) with the same subscripts can be joined together. Cooling water connections at the combustion chambers and condensers are identified by (w), and vacuum connections at the receivers are identified by (v). The receivers (measuring flasks) for the combustion water are connected to the cones ($k_5$), and gas feed lines are identified by the symbols for the gases ($O_2$, $N_2$, and $H_2$) that are normally fed through them in use. The core part of the kit is the cooling part A, which in each case is connected to a suitable combustion chamber and to one of the separating receivers.

The combustion chambers B and C are available for combustion of gases and organic liquids. Gaseous and thin liquid samples are fed by the suction burner D with adjustable annular clearance.

For combustion of solid parts, the combustion chamber E (having a vortex chamber and a combustion chamber without water cooling) and the sample container F (having a gasification chamber and a pyrolysis chamber) are generally connected to the burner L and to the cooling part A. For absorption, the long separating receiver I is used. It allows a continuous operation—i.e., after combustion of a sample is completed, the low pressure in the apparatus does not have to be suspended for changing of the receiver at $k_5$. The long separating receiver I can be made to operate both as a separating and as an absorption receiver. For absorption of combustion gases with small chlorine or sulphur concentrations, the short separating receiver H operating especially according to the separation principle, which also allows a continuous operation, can also be used.

The advantages attained with the invention are the following:

the combustion apparatus assembled from the parts of the kit can be quickly rearranged in case of changing tasks;

the space requirement for the combustion, cooling, and absorption parts, which are arranged parallel to one another, is small;

for combustion of gaseous, liquid, and solid samples, the optimal apparatus in each can easily be constructed;

even samples in which much soot develops or in which deposits originate can be burned perfectly and easily;

damage of the quartz parts by corrosion is largely prevented; and all combustions can be performed with one burner—namely the suction burner D.

The following apparatuses can, for example, be constructed with the kit.

EXAMPLE 1

Apparatus for Combustion of Gases and Thin Liquid Samples

Figure 2:
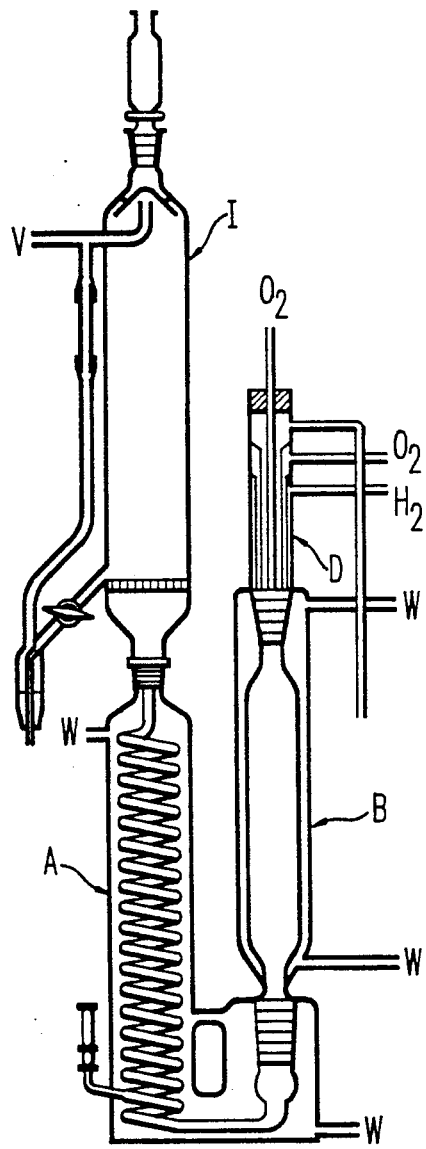
FIG. 2 shows a first arrangement of some of the components of the kit.

FIG. 2 shows the apparatus suitable for this purpose. The combustion chamber B is connected to the cooling part A and the long separating receiver I. The samples are burned with a suction burner D. In the case of gases, the sample container is securely connected to the suction capillaries. Liquids are suctioned from an open container.

EXAMPLE 2

Apparatus for Combustion of Special Liquids

Figure 3:
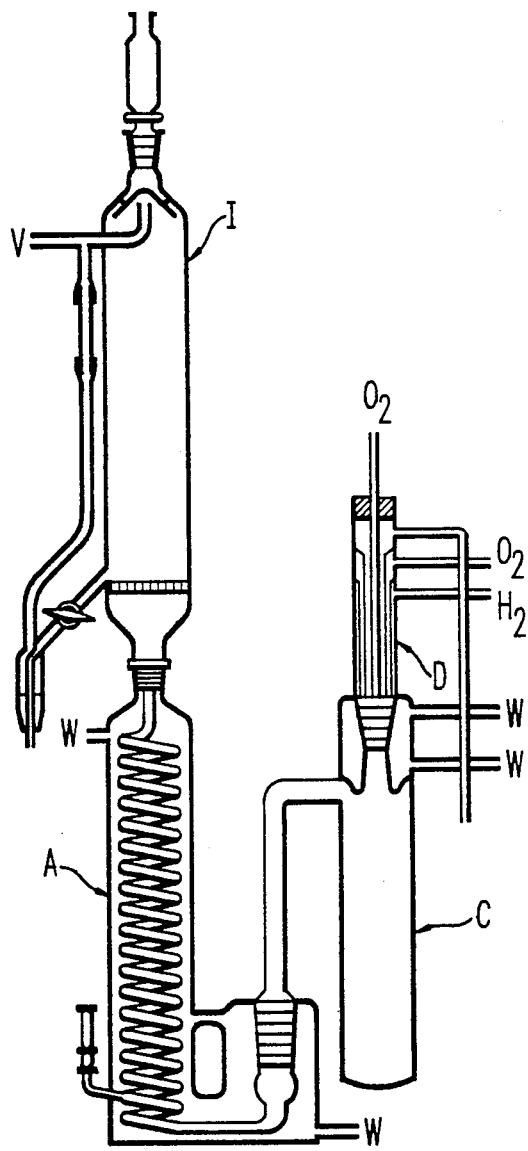
FIG. 3 shows a second arrangement of some of the components of the kit.

For thin liquid samples during the combustion of which much soot is developed or solids are formed (e.g., organometallic compounds), the apparatus represented in FIG. 3 is used. The combustion chamber C is connected to the cooling part A and to the long separating receiver I. The sample is burned with a suction burner D.

In this case, only the socket of the combustion chamber C that receives the burner D is cooled. During operation, the flame almost completely fills the combustion chamber and greatly heats the walls. Soot particles and slightly combustible material, which otherwise would deposit on the cooled walls, are completely burned in this fashion.

During combustion of organometallic compounds, a metal coating is deposited on the walls of the combustion chamber. This coating can easily be dissolved with a suitable acid after the treatment. An entrainment with the combustion gases and thus contamination and clogging of the separating receiver, as is possible in the case of the usual Wickbold apparatus, does not occur.

EXAMPLE 3

Apparatus for Combustion of Silicon-Containing Compounds

Figure 4:
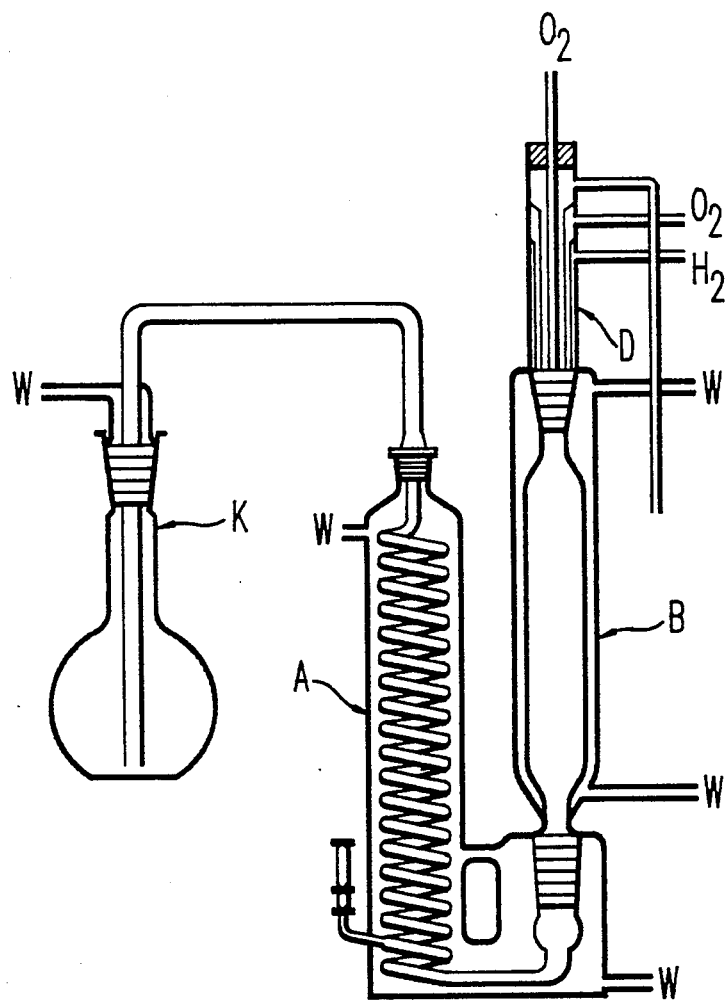
FIG. 4 shows a third arrangement of some of the components of the kit.

In FIG. 4 an apparatus is illustrated that is suitable for combustion of silicon-containing compounds. For example, during the combustion of silylated polyols, $SiO_2$ is formed in extremely finely divided form. In the case of known apparatus, the $SiO_2$ can spread in considerable amount up into the receiver. Thus, there is the danger of an absorption of the elements to be determined, and determination errors are to be expected.

This trouble can be avoided with the apparatus according to FIG. 4 if the sample, dissolved in a suitable solvent, is burned together with a fluorodonor (e.g., hydrofluoric acid). The mixture of the sample and hydrofluoric acid is burned with the suction burner D in the combustion chamber B. The combustion chamber B is connected to the cooling part A and by the vacuum adapter K to a receiver made of polyethylene or polytetrafluoroethylene.

As tests in an apparatus with the adapter and receiver made of soft soda glass have shown, the excess hydrofluoric acid attacks practically only the adapter and the receiver.

EXAMPLE 4

Apparatus for Combustion of Solids and Viscous Liquids

Figures 5, 6:
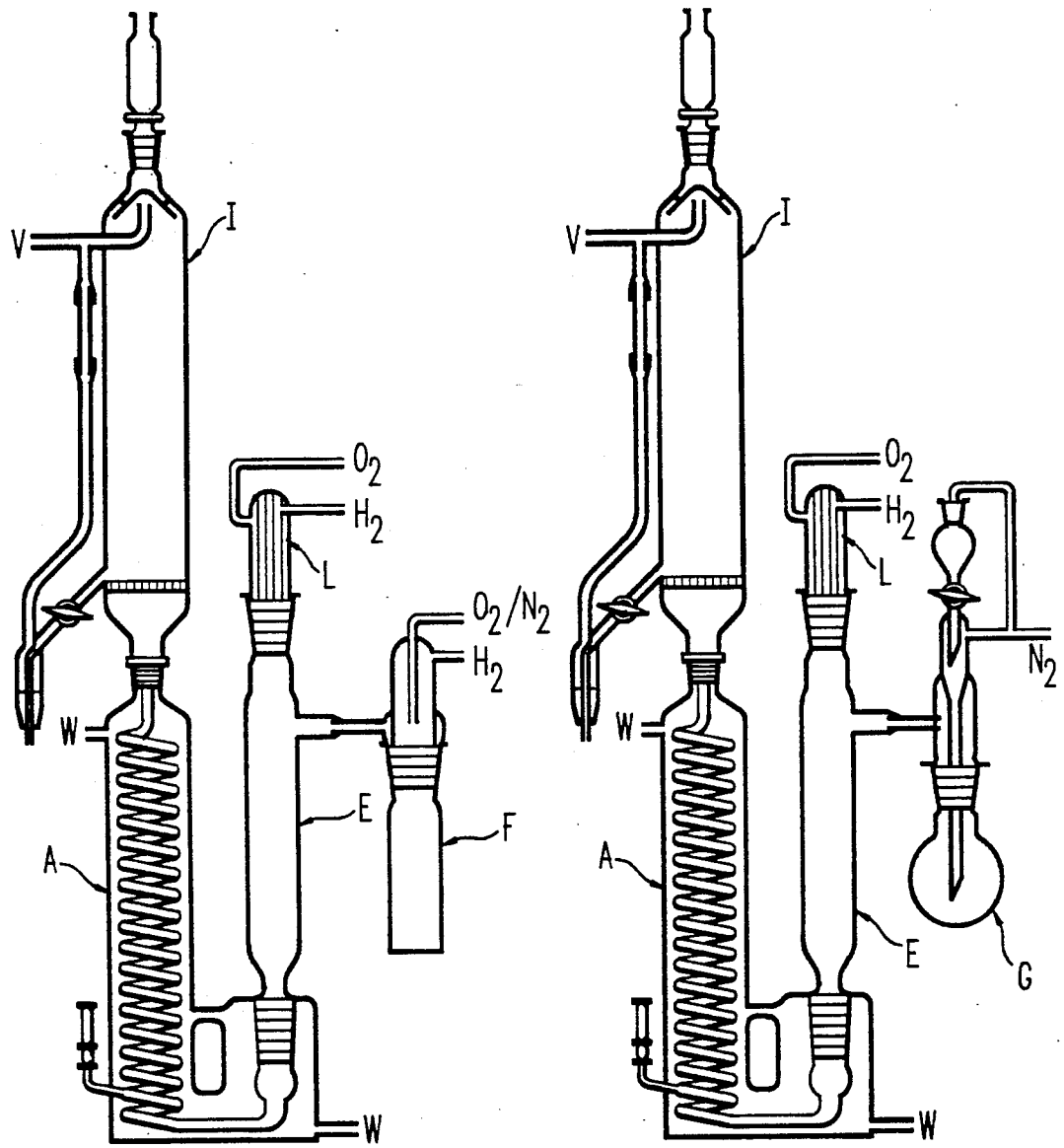
FIG. 5 shows a fourth arrangement of some of the components of the kit.
FIG. 6 shows a fifth arrangement of some of the components of the kit.

FIG. 5 shows the apparatus suitable for combustion of solids. For combustion of solid samples, the sample container F (which at the same time serves for evaporation, gasification, and pyrolysis) is connected to the combustion chamber E, the burner L, the cooling part A, and the long separating receiver I.

This apparatus is operated, for example, as follows: first the burner L is lit outside the apparatus and inserted into the socket $h_2$. Then nitrogen is passed into the sample container F containing the sample. At this point, the hydrogen feed to the sample container F is somewhat open, and thus the diffusion of vapors into the $H_2$ line is prevented. By heating of the sample container F from the outside, the sample is first carbonized, and the carbonization gases are burned in the combustion chamber E in the excess oxygen. Then the gas feed to the sample container F of nitrogen is switched to pure oxygen, and the remaining cracked residue is burned. Finally, the hydrogen feed to the sample container F is increased to the extent that the oxyhydrogen gas flame arising there conically fills the entire sample space. The superheated steam resulting thereby quantitatively drives out the residual inorganically bound halogens remaining in the ash (pyrohydrolysis).

A further possibility of using the apparatus according to FIG. 5 consists in the fact that, apart from mixed organic-inorganic samples, also purely inorganic samples can be decomposed for determination of anions (as, e.g., $Cl^-$, $F^-$) by pyrohydrolysis. The anions are converted into the forms of free acids in the long separating receiver I.

EXAMPLE 5

Apparatus for Combustion of Boric Acid Methyl Ester (Boron Determination in Solids)

The apparatus represented in FIG. 6 is suited particularly for boron determination after esterification to boric acid methyl ester. This apparatus consists of the sample container G, the combustion chamber E, the burner L, the cooling part A, and the long separating receiver I made of quartz.

For a determination of boron in solids, the sample is weighed in the sample container G. The burner L is lit outside the apparatus and inserted into the combustion chamber E. The nitrogen feed is turned on, and the sample container G with attachment is connected to the combustion chamber E. First methanol and then drop-by-drop concentrated sulfuric acid are added by a dropping funnel. The boric acid methyl ester that is formed is driven out by heating under constant passing through of nitrogen. In the combustion chamber E, the ester is converted to boric acid. The boric acid is collected in the long separating receiver I, which is charged with sodium hydroxide solution as the absorption solution.

What is claimed as new and desired to be secured by Letters Patent of the United States is:

1. A kit from which several different forms of Wickbold combustion apparatus may be formed, said kit comprising a plurality of parts as follows:
   (a) a plurality of combustion chambers;
   (b) a U-shaped cooling part containing a coil condenser having an axis, at least some parts of said U-shaped cooling part coming in contact with combustion gas during use of a Wickbold combustion apparatus formed from said kit;
   (c) a plurality of separating receivers each one of which has an inside space; and
   (d) a plurality of sample containers;
   (e) the parts of said kit recited in paragraphs (a)–(d) having corresponding sockets and cones sized, shaped, and positioned so that the parts are joinable together in a modular manner;
   (f) at least one said plurality of combustion chambers having a burner from which gas comes in a downward direction during use of a Wickbold combustion apparatus formed from said kit;
   (g) said U-shaped cooling part having a gas intake having an axis that runs parallel to the axis of said coil condenser;
   (h) at least the parts of said U-shaped cooling part coming in contact with the combustion gas during use of a Wickbold combustion apparatus formed from said kit being made of quartz and being arranged for cooling with water;
   (i) a gas outlet opening into at last one of said plurality of combustion chambers, said gas outlet being fastened to a first end of said at least one of said plurality of combustion chambers and a gas intake opening being fastened to the first end of said at least one said plurality of combustion chambers, whereby said gas intake opening is arranged for cooling with water; and
   (j) at least one of said plurality of separating receivers including an overflow device comprising a pipe between the connection to said at least one of said plurality of separating receivers and the inside space of said at least one of said plurality of separating receivers.

2. A kit according to claim 1 wherein said at least one of said plurality of combustion chambers is made of quartz.

3. A kit from which several different forms of Wickbold combustion apparatus may be formed, said kit comprising a plurality of parts as follows:
   (a) a plurality of combustion chambers;
   (b) a U-shaped cooling part containing a coil condenser having an axis, at least some parts of said U-shaped cooling part coming in contact with combustion gas during use of a Wickbold combustion apparatus formed from said kit;
   (c) a plurality of separating receivers each one of which has an inside space; and
   (d) a plurality of sample containers;
   (e) the parts of said kit recited in paragraphs (a) through (d) having corresponding sockets and cones sized, shaped, and positioned so that the parts are joinable together in a modular manner.

4. A kit according to claim 3 wherein at least one of said plurality of combustion chambers has a burner from which gas comes in a downward direction during use of a Wickbold combustion apparatus formed from said kit.

5. A kit according to claim 3 wherein:
   (a) said U-shaped cooling part has a gas intake having an axis that turns parallel to the axis of said coil condenser;

(b) at least the parts of said U-shaped cooling part coming in contact with combustion gas are made of quartz and are arranged for cooling with water;

(c) a gas outlet opens into at least one of said plurality of combustion chambers, said gas outlet being fastened to a first end of said at least one of said plurality of combustion chambers and a gas intake opening being fastened to the first end of said at least one of said plurality of combustion chambers, whereby said gas intake opening is arranged for cooling with water; and (d) at least one of said plurality of separating receivers includes an overflow device comprising a pipe between the connection to said at least one of said plurality of separating receivers and the inside space of said at least one of said plurality of separating receivers.

6. A kit according to claim 5 wherein said at least one of said plurality of combustion chambers is made of quartz.

* * * * *